United States Patent [19]

Sugano et al.

[11] Patent Number: 4,711,878
[45] Date of Patent: Dec. 8, 1987

[54] NOVEL PEPTIDES AND PROCESSES FOR PREPARING THE SAME

[75] Inventors: Hiroshi Sugano, Nara; Ryuichi Ishida, Suita; Michio Yamamura, Tondabayashi, all of Japan

[73] Assignee: Tanabe Seiyaku Co., Ltd., Osaka, Japan

[21] Appl. No.: 826,265

[22] Filed: Feb. 5, 1986

[30] Foreign Application Priority Data

Feb. 20, 1985 [GB] United Kingdom .................. 8504357

[51] Int. Cl.$^4$ ...................... A61K 37/24; C07K 7/02; C07K 5/08
[52] U.S. Cl. ..................................... 514/18; 530/331; 530/332
[58] Field of Search ................... 514/18; 530/331, 332

[56] References Cited

U.S. PATENT DOCUMENTS

| | | | |
|---|---|---|---|
| 4,045,556 | 8/1977 | Schwertner et al. | 514/19 |
| 4,059,692 | 11/1977 | Takahashi et al. | 514/18 |
| 4,100,152 | 7/1973 | Fujino et al. | 548/336 |

*Primary Examiner*—Delbert R. Phillips
*Attorney, Agent, or Firm*—Birch, Stewart, Kolasch & Birch

[57] ABSTRACT

Novel peptides of the formula:

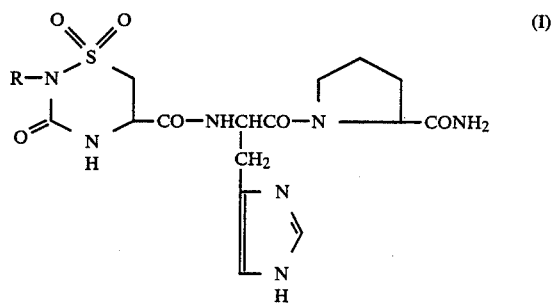

wherein R is hydrogen or a lower alkyl group, or a pharmaceutically acceptable salt thereof, and processes for preparing the same are disclosed. The peptides and pharmaceutically acceptable salts thereof are useful for the treatment of central nervous system disorders.

8 Claims, No Drawings

NOVEL PEPTIDES AND PROCESSES FOR PREPARING THE SAME

This invention relates to novel peptides of the formula:

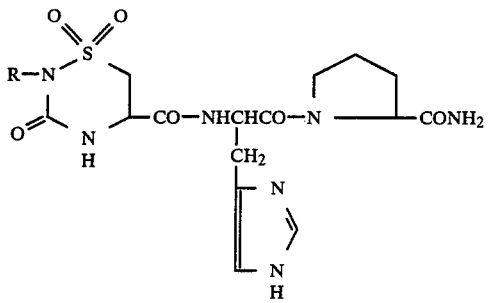

wherein R is a hydrogen or lower alkyl group, or pharmaceutically acceptable salts thereof.

It is known that TRH (i.e., thyrotropin releasing hormone; L-pyroglutamyl-L-histidyl-L-prolinamide) is useful as a medicine for treating consciousness disorders due to a brain dysfunction; but at the same time it possesses the TSH (thyroid stimulating hormone)-releasing activity, which is considered to be an undesirable action for its therapeutic effect on consciousness disorders.

As a result of various investigations, we have now found that the compound (I) of the present invention is useful as a medicine for treatment or prophylaxis of central nervous system disorders (e.g., consciousness disorder). Namely, the compound (I) of the invention is quite characteristic in that it shows much stronger activating effect upon the central nervous system (e.g., antagonistic effect on pentobarbital anesthesia, increasing effect on spontaneous locomotor activity, antagonistic effect on reserpine-induced hypothermia, potentiating effect on action of L-Dopa) with relatively less side effects (e.g., TSH-releasing activity) as compared with TRH.

According to the present invention, the compound (I) or a pharmaceutically acceptable salt thereof can be prepared by the step or steps of:

(A) condensing a compound of the formula:

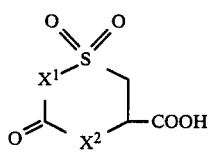

wherein $X^1$ is an imino group, a protected imino group or a lower alkyl group and $X^2$ is an imino group or a protected imino group, a salt thereof or a reactive derivative thereof with a histidyl-prolinamide compound of the formula:

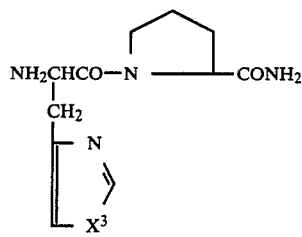

wherein $X^3$ is an imino group or a protected imino group, or a salt thereof, or (B) condensing a compound of the formula:

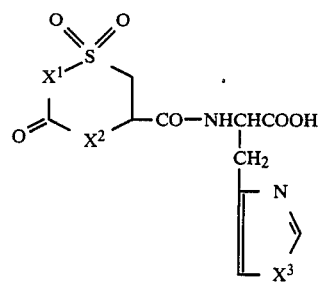

wherein $X^1$, $X^2$ and $X^3$ are the same as defined above, a salt thereof or a reactive derivative thereof with a prolinamide of the formula:

or a salt thereof, or (C) converting a compound of the formula :

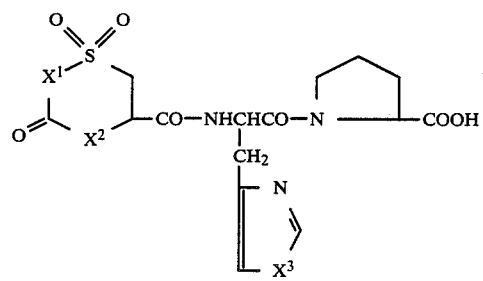

wherein $X^1$, $X^2$ and $X^3$ are the same as defined above, a salt thereof or a reactive derivative thereof into the corresponding amide thereof, (D) when at least either one of $X^1$, $X^2$ and $X^3$ of the product obtained in the reaction step (A), (B) or (C) is the protected imino group, removing the protecting group therefrom, and (E) if required, further converting the product into a pharmaceutically acceptable salt thereof.

The starting compounds (II)–(VI) may be used either in free form or in the form of a salt thereof. Examples of the salt of the compounds (II)–(VI) include inorganic acid addition salts such as hydrochloride, hydrobromide, sulfate or nitrate, organic acid addition salts such as tosylate, methanesulfonate or trifluoroacetate, and so forth.

Suitable examples of the reactive derivative of the compound (II), (IV) or (VI) include the corresponding acid halides (e.g., chloride, bromide), mixed anhydrides (e.g., a mixed anhydride with alkyl carbonate), active esters (e.g., ester with pentachlorophenol, p-nitrophenol, 2,4,6-trinitrophenol, N-hydroxy-succinimide) acid azide and other reactive derivatives such as amide with imidazole, 4-substituted-imidazole or triazole. Esters such as alkyl esters (e.g., methyl or ethyl ester) and aralkyl esters (e.g., benzyl ester) may also be used as the reactive derivative of the compound (VI).

On the other hand, a wide variety of protecting groups which have been usually employed to protect imino group or groups in the peptide synthesis can be used as the protecting group or groups $X^1$, $X^2$ and/or $X^3$. Examples of such protecting groups $X^1$, $X^2$ and $X^3$ include lower of such protecting groups X alkanoyl such as formyl, acetyl and propionyl; substituted or unsubstituted benzoyl such as benzoyl; lower alkoxycarbonyl such as methoxycarbonyl, ethoxycarbonyl, and tert-butoxycarbonyl; mono-, di- or triharoganolower alkoxycarbonyl such as 2,2,2-trichloroethoxycarbonyl; substituted or unsubstituted benzyloxycarbonyl such as benzyloxycarbonyl and p-methoxybenzyloxycarbonyl; substituted or unsubstituted phenyl-lower alkyl such as benzyl, p-methoxybenzyl and 3,4-dimethoxy-benzyl; di- or triphenyl-lower alkyl such as benzhydryl and trityl; substituted or unsubstituted phenylsulfonyl such as tosyl; substituted or unsubstituted phenylsulfenyl such as o-nitrophenylsulfenyl; and the like.

Reaction Steps (A) and (B)

The condensation of the compound (II), a salt thereof or a reactive derivative thereof with the compound (III) or a salt thereof and the condensation of the compound (IV), a salt thereof or a reactive derivative thereof with the compound (V) or a salt thereof can be accomplished in conventional manners for the synthesis of peptides. For example, the condensation reaction of the reactive derivative of the compound (II) with the compound (III) or a salt thereof and the condensation reaction of the reactive derivative of the compound (IV) with the compound (V) or a salt thereof can be conducted either in the presence or absence of an acid acceptor in a solvent. Suitable examples of the acid acceptor include alkali metal hydroxides (e.g., potassium hydroxide, sodium hydroxide), alkali metal carbonates (e.g., sodium carbonate, potassium carbonate), alkali metal bicarbonates (e.g., sodium bicarbonate, potassium bicarbonate), trialkyl aines (e.g., trimethylamine, triethylamine), N,N-dialkylanilines (e.g., N,N-dimethylaniline, N,N-diethylaniline), pyridine, N-alkylmorpholines (e.g., N-methylmorpholine), and so forth. Dioxane, tetrahydrofuran, acetonitrile, methylene chloride, dimethylformamide, dimethylacetamide, ethyl acetate, pyridine, acetone and water are suitable as the solvent. It is preferred to carry out the reaction at a temperature of −30° to 50° C., especially at −10° to 10° C.

On the other hand, the condensation reaction of the compound (II) in its free form or a salt thereof with the compound (III) or a salt thereof and the condensation reaction of the compound (IV) in its free form or a salt thereof with the compound (V) or a salt thereof can be conducted in the presence of a dehydrating agent in a solvent. Suitable examples of the dehydrating agent include dicyclohexylcarbodiimide, N-cyclohexyl-N'morpholinocarbodiimide, N-ethyl-N'-(3-dimethylaminopropyl) carbodiimide, phosphorus oxychloride, phosphorus trichloride, thionyl chloride, oxalyl chloride, triphenylphosphine and the like. Vilsmeier reagent prepared from dimethylformamide and phosphorus oxychloride, from dimethylformamide and oxalyl chloride, from dimethylformamide and phosgen or from dimethylformamide and thionyl chloride may also be used as said dehydrating agent. It is preferred to carry out the reaction at a temperature of −50° to 50° C., especially at −10° to 10° C. Dioxane, tetrahydrofuran, acetonitrile, chloroform, methylene chloride, dimethylformamide, N,N-dimethylacetamide, ethyl acetate, pyridine, acetone and water are suitable as the solvent.

Reaction Step (C)

The conversion of the compound (VI), a salt thereof or a reactive derivative thereof into the corresponding amide thereof can be conducted in a conventional manner, i.e., by treatment with ammonia or an ammonia-releasing substance. For example, this amidation is carried out by treating the compound (VI) or a salt thereof with ammonia or an ammonia-releasing substance in the presence of a dehydrating agent in a solvent. Any compounds which generate or release ammonia in the reaction solution may be used as the ammonia-releasing substance of the invention. Such ammonia-releasing substance includes, for example, ammonium chloride, ammonium carbonate and the like. The same dehydrating agents as mentioned in the reaction steps (A) and (B) may also be used in this step. It is preferred to carry out the reaction at a temperature of −20° to 20° C., especially at −5° to 5° C. Dimethyformamide, dimethylsulfoxide and tetrahydrofuran are suitable as the solvent.

The amidation is also carried out, for example, by treating the reactive derivative of the compound (VI) with ammonia or an ammonia-releasing substance in the presence or absence of an acid acceptor in a solvent. The same acid acceptors as mentioned in the reaction steps (A) and (B) may also be used in this step. It is preferred to carry out the reaction at a temperature of −20° to 20° C. Methanol, ethanol, dimethylformamide and dimethylsulfoxide are suitable as the solvent.

Reaction Step (D)

When $X^1$, $X^2$ and/or $X^3$ of the product obtained in the step (A), (B) or (C) is (or are) the protecting group or groups, said protecting group or groups may be readily removed from the product in conventional manners. For example, the removal of the protecting group or groups may be conducted by hydrolysis, electrolysis, base treatment, acid treatment, reduction, oxidation or any combination thereof. More specifically, for example, when the protecting group is benzoyl, said group may be removed by treating the compound with a base. Suitable examples of such base include ammonia, mono- or di- lower alkyl amine (lower-alkyl group in this case is, for example, methyl, ethyl, isopropyl or n-butyl) and sodium alkoxide (e.g., sodium methoxide, sodium ethoxide). This reaction may be conducted with or without a solvent(e.g., methanol, ethanol) at a temperature of −5° to 0° C. When the protecting group is benzoyl, acetyl, tert.-butoxycarbonyl, benzhyryl, trityl or o-nitrophenylsulphenyl, said group may be removed by treating the compound with an acid. Suitable examples of such an acid include formic acid, trifluoroacetic acid, benzenesulfonic acid, p-toluenesulfonic acid, hydrogen chloride or hydrogen bromide. This reaction may be conducted with or without a solvent (e.g., water, methanol, ethanol, acetic acid or dioxane) at a temperature of −30° to 70° C. When the protecting group is benzyloxycarbonyl, p-methoxybenzyloxycarbonyl, benzyl or p-methoxyenzyl, the removal of said protecting group may be conducted by catalytic hydrogenation. This catalytic hydrogenation is preferably carried out at a temperature of 0° to 100° C., and preferred examples of the catalyst include palladium-BaCO₃, palladium-charcoal and palladium-black. Methanol, ethanol, tetrahydrofuran and water are suitable as the raaction solvent. When the protecting group is methoxycarbonyl or ethoxycarbonyl, said group may be removed by hydrolysis of the compound or by base treatment thereof. The hydrolysis can be carried out in conventional manners, for example, by treating it with a base such as potassium hydroxide or an acid such as hydrochloric acid or hydrobromic acid. It is preferred to carry out said hydrolysis at a temperature of 0° to 70° C. When the protecting group is tosyl, said group may be removed by electrolysis, base treatment or treating with 1-hydroxybenzotriazole.

Reaction Step (E)

The product thus obtained in the above-mentioned reaction step and steps may be converted, if required, into a pharmaceutically acceptable salt thereof by treating it with the stoichiometrically equimolar amount of an acid in accordance with conventional manners.

In the above-mentioned reactions, the starting compounds (II)–(VI) may be used in the form of either an optically active isomer or a mixture thereof. Since the reactions of the invention proceed without racemization, the compound (I) is readily obtained in the form of an optically active isomer by the use of the corresponding optically active isomers of the compounds (II)–(VI).

Among the starting compounds, compound (I) in which $X^1$ and $X^2$ are imino groups may be prepared, for example, according to the method described in J. Med. Chem., 27, 228 (1984). On the other hand, the compound (II) in which $X^1$ is a lower alkylimino and $X^2$ is imino group may be prepared according to the following Scheme 1.

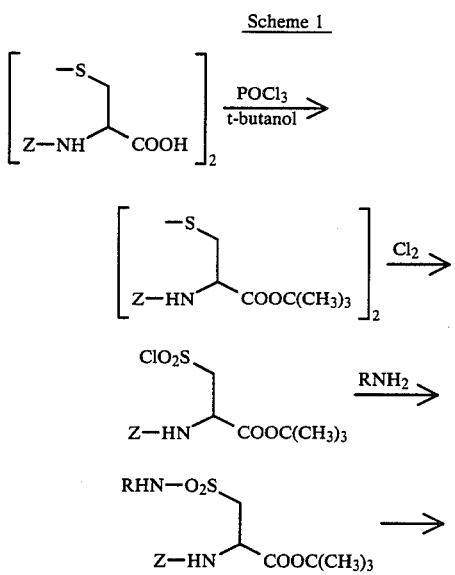

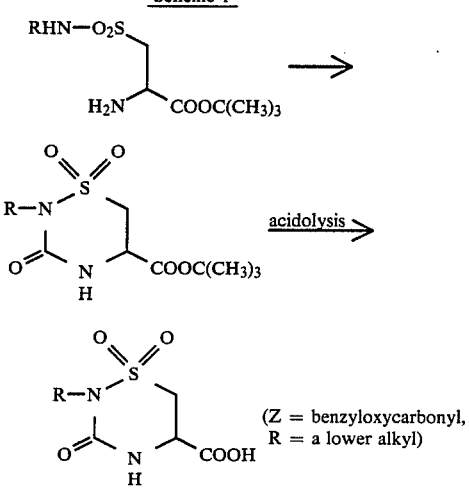

(Z = benzyloxycarbonyl, R = a lower alkyl)

Further, if required, the protecting group or groups may be introduced into the compound (II) (wherein $X^1$ and/or $X^2$ is (or are) imino group or groups) according to a conventional manner.

The compound (IV) may be prepared by condensing the compound (II) with histidine or $N^{im}$-protected histidine according to a conventional manner for peptide synthesis. Moreover, the compound (VI) may be prepared by condensing the compound (II) with histidyl-proline or the compond (IV) with proline according to a conventional manner for peptide synthesis.

The compound (I) of the present invention can exist in the form of eight optical isomers due to the three asymmetric carbon atoms involved therein, and all of the eight optical isomers or a mixture thereof are included within the scope of the invention.

Among those isomers, however, the compounds wherein the histidyl and prolyl groups are in L-configuration are especially preferred for medicinal use.

The compound (I) can be used for pharmaceutical use either as the free base or as an acid addition salt thereof. Pharmaceutically acceptable acid addition salts of the compound (I) are, for example, inorganic acid addition salts such as hydrochloride, hydrobromide, sulfate or nitrate; and organic acid addition salts such as acetate, maleate, tartrate, succinate, citrate, methanesulfonate, malate, oxalate or benzenesulfonate. These salts may be prepared, for example, by neutralizing the compound (I) with an acid.

The compound (I) or a pharmaceutically acceptable acid addition salt thereof may be administered either orally or parenterally to a warm-blooded animal including human beings. Further, the compound (I) or a salt thereof may be used in the form of a pharmaceutical preparation containing the same compound in conjunction or admixture with a pharmaceutical excipient suitable for oral or parenteral administration. Suitable excipients are, for example, starch, lactose, glucose, potassium phosphate, corn starch, arabic gum, stearic acid or other known medicinal excipients. The pharmaceutical preparation may be in solid form such as, for example, tablets, powders, capsules or granules; or in liquid form such as, for example, solutions or suspensions. Further, when administered parenterally, the pharmaceutical preparation may be used in the form of injections.

As mentioned hereinbefore, the compound (I) or a salt thereof of the present invention has much stronger activating effects upon the central nervous system (e.g., antagonistic effects on pentobarbital anesthesia, increasing effect on spontaneous locomotor activity, antagonistic effect on reserpine-induced hypothermia and potentiating effect on action of L-Dopa) with relatively less side effects (e.g., TSH-releasing activity) as compared with TRH. Therefore, the compound (I) or a salt thereof is much more useful as palinesthesias, spontaneous movement stimulants or dopamine potentiators than TRH.

The compound (I) or a salt thereof is also useful for the treatment or prophlaxis of central nervous system disorders such as, for example, consciousness disorders, short attention span, speech disorders, hypobulia, Lennox syndrome, senile dementia, hypnotic intoxication, autism, hyperkinesia, schizophrenia, depression and parkinsonism in a warm-blooded animal including human being.

The therapeutic dose of the compound (I) or a salt thereof depends on route of administration; the age, weight and condition of patients; and the particular disease to be treated. In general, however, it may be used at a dose of 0.5 μg to 5 mg per kilogram of body weight per day; especially at a dose of 10 μg to 1 mg per kilogram of body weight per day in the case of oral administration; or at a dose of 1 μg to 100 μg per kilogram of body weight per day in the case of parenteral administration (e.g., intravenously, intramuscularly, subcutaneously).

Practical and presently-prefered embodiments of the present invention are illustratively shown in the following lines.

EXPERIMENTS

The pharmacological activities of the test compounds were tested by the following method.

(Methods)

(1) Antagonistic effect on reserpine-inuced hypothermia:

Five male STD/ddY mice (6 weeks old) which showed the body temperatures of 30° C. or lower about 17 to 20 hours after subcutaneous administration of reserpine (3 mg/kg) were used in each group. A test compound dissolved in a physiological saline solution was intraperitoneally administered to the mice, and the rectal temperature was measured 30, 60, 120 and 180 minutes after the administration of the test compound. The increase in temperature of the treated group was compared with that of the control group which received a physiological saline solution instead of the test compound solution.

(2) Increasing effect on spontaneous locomotor activity:

Five male STD/ddY mice (6 weeks old) were used in each group. The mice were individually placed in Ambulometer (i.e., an apparatus for measuring spontaneous locomotor activity; manufactured by OHARA IKA Co.) for 30 minutes to acclimatize to the apparatus. Thereafter, a test compound dissolved in a physiological saline solution was intraperitoneally administered to the mice and, immediately after administration of the test compound, the spontaneous locomotor activity was measured for 60 minutes. A physiological saline solution was used for the control group instead of the test compound solution.

(3) Antagonistic effect on pentobarbital anesthesia:

Ten male STD/ddY mice (6 weeks old) were used in each group. Pentobarbital sodium was intraperitoneally administered to the mice at a dose of 55 mg/kg. Ten minutes after the administration of pentobarbital sodium, a test compound dissolved in a physiological saline solution was intravenously administered to the mice which had lost the righting reflex. The duration of anesthesia was measured as the time from the end of administration of test compound until the righting reflex regained. A physiological saline solution was used for the control group instead of the test compound solution. (Prange et al., Life Science, 14, 447–455, (1947))

(4) Potentiating effect on action of L-Dopa:

Five male STD/ddY mice (6 weeks old ) were used in each group. Reserpine was subcutaneously administered to the mice at a dose of 3 mg/kg and, about 16 to 20 hours later, L-Dopa was intraperitoneally administered to the mice at a dose of 200 mg/kg. Fifteen minutes after administration of L-Dopa, a test compound dissolved in a physiolosical saline solution was administered intraperitoneally to the mice (When TRH was used as the test compound, it was administered 25 minutes after administration of L-Dopa). Spontaneous locomotor activity was measured for 15 minutes starting from 30 minutes afer administration of L-Dopa. A physiolosical saline solution was used for the control group instead of the test compound solution (results)

The results are shown in the following Table 1.

TABLE 1

| (Pharmacological activities) | |
|---|---|
| | Potency ratio relative to TRH* $N^\alpha$—[(RS)—3-oxo-3,4,5,6-tetrahydro-2H—1,2,4-thiadiazine-1,1-dioxide-5-carbonyl]-L-histidyl-L-prolinamide |
| Antagonistic effect on reserpine-induced hypothermia | 27.1 |
| Increasing effect on spontaneous locomotor activity | 41.8 |
| Antagonistic effect on pentobarbital anesthesia | 1.6 |
| Potentiating effect on action of Dopamine | 16.2 |

Note:
*Potency ratio relative to TRH was calculated from the dose response-curves of TRH and $N^\alpha$—[(RS)—3-oxo-3,4,5,6-tetrahydro-2H—1,2,4-thiadiazine-1,1-dioxide-5-carbonyl]-L-histidyl-L-prolinamide.

EXAMPLE 1

(1) 28 g of phosphorous oxychloride are added to a mixture of 76.2 g of N,N'-dibenzyloxycarbonyl-L-cystine (Chem. Ber., 65 , 1196 (1932)), 89 g of tert-butanol, 95 g of pyridine and 800 ml of dichloroethane at −3° to 2° C. under stirring. The mixture is stirred at the same temperature for 1 hour and at room temperature for 2 hours. The reaction mixture is poured into ice-water, and the organic layer is washed with sodium bicarbonate and water, successively. The organic layer is dried and then evaporated to remove the solvent. The residue is purified by silica gel column chromatography ( solvent; chloroform:isopropyl ether=3:7 ) and recrystalized from a mixture of isopropyl ether and n-hexane. 40.2 g of N,N'-dibenzyloxycarbonyl-L-cystine di-tert-butyl ester are obtained.

M.p. 77°–78° C.

$[\alpha]_D^{19}$ −94.0° (C=0.5, methanol)

(2) A mixture of 27 g of N,N'-dibenzyloxycarbonyl-L-cystine di-tert-butyl ester, 270 ml of carbon tetrachloride and 55 ml of ethanol is saturated with $Cl_2$ gas under stirring at 0°-5° C. for 30 minutes. The mixture is stirred at room temperature for 30 minutes and then evaporated to remove the solvent. 32.8 g of [(R)-2-Tert-butyloxycarbonyl-2-benzyloxycarbonylaminoethane]-sulfonyl chloride are obtained as oil.

$IR\nu_{max}^{chloroform}(cm^{-1})$:3400, 1720

NMR $(CDCl_3,\delta)$:1.5 (s, 9H, —$(CH_3)_3$), 4.2–4.9 (m, 3H, —CH and —$CH_2$), 5.18 (s, 2H,

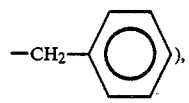

5.80 (d, 1H, NH ), 7.3–7.4 (m, 5H, arom-H)

(3) 8.2 g of [(R)-2-Tert-butyloxycarbonl-2-benzyloxycarbonylaminoethane]sulfonyl chloride are dissolved in 150 ml of tetrahydrofuran, and the solution is saturated with methylamine. The mixture is evaporated to remove tetrahydrofuran under reduced pressure. The residue is dissolved in chloroform, and the chloroform layer is washed with water. The solution is dried and evaporated to remove chloroform, and the residue is purified by silica gel column chlomatography (solvent; chloroform:diethylether=9:1). 13.3 g of N-methyl[(R)-2-tert-butyloxycarbonyl-2-benzyloxycarbonylaminoethane]sulfonamide are obtained as oil.

$IR\nu_{max}^{chloroform}(cm^{-1})$: 3400, 1720

NMR $(CDCl_2,\delta)$: 1.50 (s, 9H, —$(CH_3)_3$), 2.62 and 2.72 (2s, 3H, N—$CH_3$), 3.4–3.8 (m, 2H, $CH_2$), 5.15 (s, 2H,

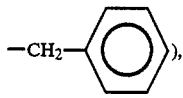

5.99 (d, 1H, NH ), 7.3–7.5 (m, 5H, arom-H )

(4) 13 g of N-methyl[(R)-2-tert-butyloxycarbonyl-2-benzyloxycarbonylaminoethane]sulfonamide are dissolved in 100 ml of methanol. 2.2 g of palladium-black are added thereto, and the mixture is shaken for 8 hours. The catalyst is filtered off, and the filtrate ts evaporated to remove the solvent. The residue is recrystallized from a mixture of methanol and chloroform. 7.9 g of N-methyl [(R)-2-tert-butyloxycarbonyl-2-aminoethane]sulfonamide hydrochloride are obtained.

M.p. 146°–147° C. (decomp.)

$[\alpha]_D^{22}+7.4°$ (C=0.5, dimethylformamide)

$IR\nu_{max}^{nujol}$ (cm$^{-1}$): 1750

NMR (DMSO-$d_6,\delta$): 1.47 (s, 9H, —$(CH_3)_3$), 2.62 (s, 3H, N—$CH_3$), 2.62 (d, 2H, —$CH_2$—, J=5 Hz ), 4.20 (t, 1H, —CH, J=5 Hz ), 7.55 (br, 1H, NH)

(5) 7.75 g of N-methyl[(R)-2-tert-butyloxycarbonyl-2-aminoethane ]sulfonamide are dissolved in a mixture of 20 ml of dimethylformamide and 80 ml of tetrahydrofurane. 12 g of carbonyldiimidazole are added thereto, and the mixture is stirred under ice-cooling for 6 days. The reaction mixture is evaporated to remove the solvent, and the residue is dissolved in 10% citric acid. The solution is extracted with ethyl acetate. The ethyl acetate layer is dried and evaporated to remove the solvent. The residue is purified by silica gel column chromatography ( solvent ; ether) and recrystallized from a mixture of chloroform and isopropyl ether. 3.4 g of Tert-butyl (R)-2-methyl-3-oxo-3,4,5,6-tetrahydro-2H-1,2,4-thiadiazine-1,1-dioxide-5-carboxylate are obtained.

M.p. 134°–135° C.

$[\alpha]_D^{21}-8.8°$ (C=0.5, dimethylformamide)

$IR\nu_{max}^{nujol}(cm^{-1})$: 3250, 1730, 1680

NMR $(CDCl_3, \delta)$: 1.52 (s, 9H, —$(CH_3)_3$), 3.20 (s, 3H, N—$CH_3$), 3.2–4.0 (m, 2H, —$CH_2$), 4.35–4.60 (m, 1H, —CH), 6.21 (s, 1H, NH)

(6) 3.4 g of Tert-butyl (R)-2methyl-3-oxo-3,4,5,6-tetrahydro-2H-1,2,4-thiadiazine-1,1-dioxide-5-carboxylate are dissolved in 50 ml of trifluoroacetic acid, and the solution is stirred at 5° C. for 2 hours. The reaction mixture is evaporated to remove trifluoroacetic acid under reduced pressure. Isopropyl ether is added to the residue, and crude crystals thus obtained are recrystallized from a mixture of methanol and isopropyl ether. 2.3 g of (R)-2- Methyl-3-oxo-3,4,5,6-tetrahydro-2H-1,2,4-thiadiazine-1,1-dioxide-5-carboxylic acid are obtained.

M.p. 202°–205° C. (decomp.)

$[\alpha]_D^{17}-12.6°$ (C=0.5, dimethylformaide)

$IR\nu_{max}^{nujol}(cm^{-1})$: 3230, 1725, 1640

NMR (DMSO-$d_6,\delta$): 2.94 (s, 3H, N—$CH_3$), 3.93 (d, 2H, $CH_2$, J=6 Hz ), 4.25–4.50 (m, 1H, CH—), 7.95 (d, 1H, NH )

(7) 1.04 g of (R)-2-Methyl-3-oxo-3,4,5,6-tetrahydro-2H-thiadiazine-1,1-dioxide-5-carboxylic acid and 640 mg of N-hydroxysuccinimide are dissolved in 10 ml of dimethylformamide, and 1.15 g of dicyclohexylcarbodiimide are added thereto at 0° C. under stirring. The mixture is stirred at room temperature for 30 minutes. (The resulting solution is hereinafter referred to "Solution A".)

On the other hand, 2.17 g of L-histidyl-L-prolinamide dihydrobromide and 1.1 g of triethylamine are dissolved in 10 ml of dimethylformamide at 0° C. Insoluble materials are filtered off, and the filtrate is added to "Solution A" prepared above. The mixture is stirred at 0° C. for 4 hours and then at 10° C. for three days. Insoluble materials are again filtered off, and the filtrate is concentrated under reduced pressure. The residue is dissolved in water, and insoluble materials are filtered off. The filtrate is passed through a column (2.6×28 cm) packed with styrene-divinylbenzene copolymer resin (manufactured by Mitsubish Chemical Industries Ltd. under the trade mark "MIC GEL CHP-20P"; hereinafter simply reffered to as "CHP-20P resin"). The column is washed with water and 30% methanol, successively. The fractions containing the desired product are collected and evaporated to remove the solvent. The residue is purified by silica gel column chromatography (solvent; chloroform:methanol=6:4). The eluate is passed through a column (2.6×28 cm) packed with CHP-20P resin. After the column is washed with water, the desired product is eluted with 40% methanol. The eluate thus obtained is concentrated and then lyophilized. 1.33 g of $N^\alpha$[(R)-2-Methyl-3-oxo-3,4,5,6-tetrahydro- 2H-1,2,4-thiadiazine-1,1-dioxide-5-carbonyl]-L-histidyl-L-prolinamide are obtained.

$[\alpha]_D^{19}-68.4°$ (C=0.5, $H_2O$)

$IR\nu_{max}^{nujol}(cm^{-1})$: 1670

NMR (DMSO-$d_6$, $\delta$): 1.6–2.3 (m, 4H, Pro $\beta,\gamma$—$CH_2$), 2.96 (s, 3H, N—$CH_2$), 2.7–4.5 (m, 8H) 4.5–4.9 (m, 1H, His$\alpha$—CH )

EXAMPLE 2

(1) 32.8 g of[(R)-2-Tert-butyloxycarbonyl-2-benzyloxycarbonylaminoethane ]sulfonyl chloride are dissolved in 300 ml of tetrahydrofurane, and the solution is saturated with $NH_3$ gas at 0°–5° C. for 30 minutes. The ammonia-saturated solution is stirred at room temperature for 30 minutes, and then evaporated to remove the solvent. The residue is dissolved in 300 ml of chloroform, and the solution is washed with water and dried. The solution is evaporated to remove chloroform, and the residue is purified by silica gel column chromatography (solvent ; chloroform:methanol=95:5). 32 g of [(R)-2-Tert-butyloxycarbonyl-2-benzyloxycabonylaminoethane]sulfonamide are obtained as oil.

$IR\nu_{max}^{chloroform}$ ($cm^{-1}$): 3400, 1720

NMR ($CDCl_3,\delta$): 1.42 (s, 9H, —$(CH_3)_3$), 3.55 (d, 2H, —$CH_2$), 4.4–4.7 (m, 1H, —CH), 5.05 (s, 2H,

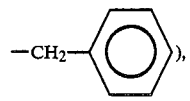

), 6.17 (s, 2H, $NH_2$), 6.68 (brd, 1H, NH ), 7.2–7.3 (m, 5H, arom-H)

(2) 32 g of[(R)-2-Tert-butyloxycarbony-2-benzyloxycarbonylaminoethane]sulfonamide are dissolved in 150 ml of ethanol, and 5 g of palladium-black are added thereto. The mixture is shaken in hydrogen gas atmosphere under the pressure of 3 kg/cm². The catalyst is filtered off, and the filtrate is evaporated to remove the solvent. 20 g of [(R)-2-Tert-butyloxycarbonyl-2-aminoethane]sulfonamide are obtained as oil.

$IR\nu_{max}^{chloroform}$($cm^{-1}$): 1735

NMR (DMSO-$d_6,\delta$): 1.45 (s, 9H, —$(CH_3)_3$), 3.54 (d, 2H, —$CH_2$, J=5 Hz ), 4.20 (t, 1H, CH, J=5 Hz )

(3) 20 g of[(R)-2-Tert-butyloxycarbonyl-2-aminoethane] sulfonamide are dissolved in 400 ml of chlorofor of carbonyldiimidazole are added thereto at 0°–5° C. The mixture is stirred at room temperature for 3 days. The chloroform soultion is washed with of water, and then dried. The solution is evaporated to remove chloroform. The crystals obtained are collected by filtration, and washed with ether. 6.91 g of Tert-butyl (R)-3-oxo-3,4,5,6-tetrahydro-2H-1,2,4-thiadiazine-1,1-dioxide-5-carboxylate are obtained.

M.p. 196°–197° C.

$[\alpha]_D^{22} -9.0°$ (C=0.5, dimethylformamide)

$IR\nu_{max}^{nujol}$ ($cm^{-1}$): 3220, 1735, 1670

NMR (DMSO-$d_6,\delta$): 1.41 (s, 9H, —$(CH_3)_3$), 3.68 (d, 2H, $CH_2$, J=5 Hz), 4.2–4.5 (m, 1H, CH ), 7.83 (d, 1H, NH )

(4) 5.0 g of Tert-butyl (R)-3-oxo-3,4,5,6-tetrahydro-2H-1,2,4-thiadiazine-1,1-dioxide-5-carboxy in 60 ml of trifluoroacetic acid, and the solution is stirred at 5° C. for 2 hours. The solution is evaporated to remove trifluroacetic acid, and ether is added to the residue. The resulting crystals are collected by filtration, and recrystallized from a mixture of methanol and ether. 3.17 g of (R)-3-Oxo-3,4,5,6-tetrahydro-2H-1,2,4-thiadiazine-1,1-dioxide-5-carboxylic acid are obtained.

M.p. 190°–191° C.

$[\alpha]_D^{19} -15.0°$ (C=0.5, dimethylformaide)

$IR\nu_{max}^{nujol}$($cm^{-1}$): 3300, 1755, 1740, 1650

NMR (DMSO-$d_6,\delta$): 3.69 (d, 2H, $CH_2$, J=5 Hz ), 4.2–4.5 (m, 1H, CH ), 7.72 (d, 1H, NH )

(5) 2.2 g of (R)-3-Oxo-3,4,5,6-tetrahydro-2H-1,2,4-thiadiazine-1,1-dioxide-5-carboxylic acid and 1.56 g of N-hydroxy-succinimide are dissolved in 20 ml of dimethylformamide. 2.8 g of Dicyclohexylcarbodiimide are added thereto at 0 ° C. The mixture is stirred at the same temperature for one hour. (The resulting solution is hereinafter referred to as "Solution B".)

On the other hand, 5.2 g of L-histidyl-L-prolinamide dihydrobromide are dissolved in 20 ml of dimethylformamide. 2.54 g of triethylamine are added thereto at 0 ° C., and insoluble materials are filtered off. The filtrate is added to "Solution.B" prepared above. The mixture is stirred at 0 ° C. for 4 hours and then at 10 ° C. for three days. After insoluble materials are again filtered off, the filtrate is evaporated to remove dimethylformamide. The residue is dissolved in water, and insoluble materials are filtered off. The filtrate is concentrated under reduced pressure, and the residue is purified by silica gel column chromatography (solvent; n-butanol:ethyl acetate: $H_2O$:acetic acid =1:1:1:1). The fractions which are positive to Pauly's reaction are collected, and evaporated to remove the solvent. The residue is purified by a column of cation exchange resin (Dowex 50WX8; 200–400 mesh, $H^+$form, 50 ml ). The column is washed with water, and eluted with 3% aquous ammonia. The fractions containing the desired product are collected and evaporated to remove the solvent. The residue thus obtained is dissolved in water. The solution is passed through a column (2.6×28 cm) packed with the CHP-20P resin and eluted with water. The fractions containing the desired product are collected and lyophilized. 2.51 g of $N^\alpha$-[(R)-3-Oxo-3,4,5,6-tetrahydro-2H-1,2,4-thiadiazine-1,1-dioxide-5-carbonyl]-L-ystidyl-L-prolinamide. 3/2$H_2O$ are obtained.

$[\alpha]_D^{19} -62.4°$ ( C=0.5, $H_2O$ )

EXAMPLE 3

2.21 g of (RS)-3-Oxo-3,4,5,6-tetrahydro-2H-1,2,4-thiadiazine-1,1-dioxide-5-carboxylic acid ( J. Med. Chem., 27, 228 (1984)) and 1.58 g of N-hydroxysuccinimide are dissolved in 40 ml of dimethylformamide, and 2.83 g of dicyclohexylcarbodiimide are added thereto under stirring at 0 ° C. ( The resulting solution is hereinafter referred to as "Solution C").

On the other hand, 4.78 g of L-histidyl-L-prolinamide dihydrobromide are dissolved in 40 ml of dimethylformamide, and 2.34 g of triethylamine are added thereto at 0 ° C. The mixture is stirred at 0 ° C. for 30 minutes, and inslouble materials are filtered off. The filtrate is added to "Solution C" obtained above, and the mixture is stirred at 0° C. for 4 hours and at 10 ° C. for 24 hours. Insoluble materials are filtered off, and the filtrate is concentrated under reducd pressure to remove solvent. 30 ml of water are added to the residue, and insoluble materials are filterd off. The filtrate is passed through a column (2.6×28 cm ) packed with CHP-20P resin, and the column is washed with water. The fractions which are positive to Pauly's reaction are collected and lyophilized. The thus obtained powder is purified by silica gel column chromatography (solvent; n-buthanol:acetic acid:ethyl acetate:$H_2O$=1:1:1:1). The eluate thus obtained is again passed through a column (2.6×28 cm) packed with CHP-20P resin, and the column is washed with water. The fractions which are positive to Pauly's reaction are collected and lyophilized. 1.35 g of $N^\alpha$-[(RS)-3-oxo-3,4,5,6-tetrahydro-2H-1,2,4-thiadiazine-1,1-dioxide-5-carbonyl]-L-histidyl-L-prolinamide monohydrate are obtained as powder.

$[\alpha]_D^{24} -64.8°$ (C=0.5, $H_2O$)

Mass (m/e): 427 (M+)

IR$\nu_{max}^{nujol}$(cm$^{-1}$): 1620-1640

NMR (DMSO-d$_6$, δ); 1.7-2.2 (m, 4H), 2.8-3.8 (m, 6H), 4.1-4.4 (m, 2H), 4.5-4.9 (m, 1H), 7.09 (br, 1H), 8.00 (s, 1H).

What we claim is:

1. A compound of the formula:

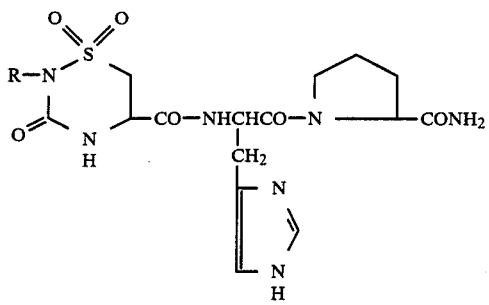 (I)

wherein R is hydrogen or a lower alkyl group, or a pharmaceutically acceptable salt thereof.

2. The compound claimed in claim 1, wherein R is hydrogen or methyl.

3. The compound claimed in claim 2, wherein the histidyl and prolyl groups are in L-configuration.

4. The compound claimed in claim 1, which is N$^\alpha$-[(R)-3-oxo-3,4,5,6-tetrahydro-2H-1,2,4-thiadiazine-1,1-dioxide-5-carbonyl]-L-histidyl-L-prolinamide or a pharmaceutically acceptable salt thereof.

5. The compound claimed in claim 1, which is N$^\alpha$-[(R)-2-methyl-3-oxo-3,4,5,6-tetrahydro-2H-1,2,4-thiadiazine-1,1dioxide-5-carbonyl-L-histidyl-L-prolinamide or pharmaceutically acceptable salt thereof.

6. The compound claimed in claim 1, which is N$^\alpha$-[(RS)- 3oxo-3,4,5,6-tetrahydro-2H-1,2,4-thiadiazine-1,1-dioxide-5-carbonyl]-L-histidyl-L-prolinamide or a pharmaceutically acceptable salt thereof.

7. A pharmaceutical composition which comprises in an effective amount for treatment or prophylaxis of a consciousness disorder in a warm blooded animal, the compound claimed in claim 1 or a pharmaceutically acceptable acid addition salt thereof and a pharmaceutically acceptable carrier therefor.

8. A method for the treatment of prophylaxis of a consciousness disorder in a warm blooded animal, which comprises administering to said warm blooded animal a therapeutically or prophylactically effective amount of the compound of claim 1 or a pharmaceutically acceptable acid addition salt thereof.

* * * * *